(12) United States Patent
Cornish et al.

(10) Patent No.: US 8,703,699 B2
(45) Date of Patent: Apr. 22, 2014

(54) LACTOFERRIN

(75) Inventors: Jillian Cornish, Auckland (NZ); Ian Reginald Reid, Auckland (NZ); Kate Patricia Palmano, Palmerston North (NZ); Neill Ward Haggarty, Palmerston North (NZ)

(73) Assignee: Auckland Uniservices Limited, Auckland (NZ)

( * ) Notice: Subject to any disclaimer, the term of this patent is extended or adjusted under 35 U.S.C. 154(b) by 0 days.

(21) Appl. No.: 13/082,334

(22) Filed: Apr. 7, 2011

(65) Prior Publication Data

US 2011/0183008 A1 Jul. 28, 2011

Related U.S. Application Data

(63) Continuation of application No. 12/853,149, filed on Aug. 9, 2010, now abandoned, which is a continuation of application No. 12/493,919, filed on Jun. 29, 2009, now abandoned, which is a continuation of application No. 12/098,253, filed on Apr. 4, 2008, now abandoned, which is a continuation of application No. 10/205,960, filed on Jul. 26, 2002, now abandoned.

(30) Foreign Application Priority Data

Apr. 3, 2002 (NZ) .......................... 518121

(51) Int. Cl.
 *A61K 38/40* (2006.01)
 *C07K 14/79* (2006.01)
 *A61K 38/00* (2006.01)

(52) U.S. Cl.
 USPC .............................. 514/2.5; 530/395; 514/1.1

(58) Field of Classification Search
 None
 See application file for complete search history.

(56) References Cited

U.S. PATENT DOCUMENTS

| 5,240,909 | A | * | 8/1993 | Nitsche | 514/8 |
| 5,596,082 | A | * | 1/1997 | Kussendrager et al. | 530/416 |
| 5,932,259 | A | * | 8/1999 | Kato et al. | 426/42 |
| 6,251,860 | B1 | | 6/2001 | Parkkinen et al. | |
| 6,440,446 | B1 | * | 8/2002 | Yoshizane et al. | 424/423 |
| 2002/0004073 | A1 | | 1/2002 | Gohlke et al. | |
| 2003/0154032 | A1 | | 8/2003 | Pittman et al. | |
| 2011/0183008 | A1 | * | 7/2011 | Cornish et al. | 424/641 |

FOREIGN PATENT DOCUMENTS

| AU | 760503 | | 11/1999 | |
| EP | 0426924 A1 | | 4/1991 | |
| EP | 0 584 558 | | 3/1994 | |
| EP | 0 704 218 | | 4/1996 | |
| EP | 0 786 473 | | 7/1997 | |
| EP | 1 116 490 | | 7/2001 | |
| JP | 63022525 | | 1/1988 | |
| JP | 2191205 | | 7/1990 | |
| JP | 2000-281586 | * | 10/2000 | A61K 38/16 |
| WO | WO 98/06424 | | 2/1998 | |
| WO | WO 98/06425 | | 2/1998 | |

OTHER PUBLICATIONS

T. G. Kanyshkova, et al. *Lactoferrin and Its Biological Functions.* Biochemistry (Moscow) 66(1):1-7, 2001—translated from Biokhimiya 66(1):5-13, 2001.
Aoe S et al., "Bone strengthening agent for preventing or treating osteoporosis, comprises active ingredient containing iron-lactoferrin having three atoms of iron per unimolecule of lactoferrin", vol. 2001, No. 8 (2000) XP002478108.
Bharadwaj et al., "Milk ribonuclease-enriched lactoferrin induces positive effects on bone turnover markers in postmenopausal women", Osteoporos Int., vol. 20, pp. 1603-1611 (2009).
Cornish et al., "Lactoferrin and bone; structure-activity relationships", Biochem. Cell Biol., vol. 84, pp. 297-302 (2006).
Lacromin™ Product Specifications, "Lacromin™ (Recombiant Human Lactoferrin-Holo)", InVitria, 1 page, (Jul. 2010).
Sarelli et al., "Lactoferrin to prevent experimental *Escherichia coli* diarrhea in weaned pigs", Int J. Applied Res. Vet. Med., Online article downloaded from http://www.jarvm.com/articles/Vol1Iss4/Heinonen.htm on Nov. 15, 2013, 6 pges. (2013).

\* cited by examiner

*Primary Examiner* — Maury Audet
(74) *Attorney, Agent, or Firm* — Susan J. Myers Fitch; McDermott Will & Emery LLP

(57) ABSTRACT

A pure lactoferrin polypeptide containing no more than two metal ions per molecule, or a mixture of the polypeptide and a fragment thereof. The polypeptide or the mixture stimulates skeletal growth and inhibits bone resorption. Also disclosed is a method of treating a bone-related disorder with the polypeptide or the mixture.

18 Claims, No Drawings

LACTOFERRIN

RELATED APPLICATION

This application is a continuation of U.S. application Ser. No. 12/853,149, filed Aug. 9, 2010 now abandoned, which is a continuation of U.S. application Ser. No. 12/493,919 now abandoned, filed Jun. 29, 2009 now abandoned, which is a continuation of U.S. application Ser. No. 12/098,253, filed Apr. 4, 2008 now abandoned, which is a continuation of U.S. application Ser. No. 10/205,960 now abandoned, filed Jul. 26, 2002 now abandoned, which claims priority to New Zealand Application Serial No. 518121, filed Apr. 3, 2002, the contents of which are incorporated herein by reference.

BACKGROUND

Lactoferrin is an 80 kD iron-binding glycoprotein present in most exocrine fluids, including tears, bile, bronchial mucus, gastrointestinal fluids, cervico-vaginal mucus, seminal fluid, and milk. It is a major constituent of the secondary specific granules of circulating poly-morphonuclear neutrophils. The richest source of lactoferrin is mammalian milk and colostrum.

Lactoferrin circulates at a concentration of 2-7 µg/ml. It has multiple postulated biological roles, including regulation of iron metabolism, immune function, and embryonic development. Lactoferrin has anti-microbial activity against a range of pathogens including Gram positive and Gram negative bacteria, yeasts, and fungi. The anti-microbial effect of lactoferrin is based on its capability of binding iron, which is essential for the growth of the pathogens. Lactoferrin also inhibits the replication of several viruses and increases the susceptibility of some bacteria to antibiotics and lysozyme by binding to lipid A component of lipopolysaccharides on bacterial membranes.

SUMMARY

This invention relates to a lactoferrin polypeptide that is capable of stimulating skeletal growth and inhibiting bone resorption.

Specifically, this invention features a pure lactoferrin polypeptide containing no more than two (i.e., 0, 1, or, preferably, 2) metal ions per molecule. A "pure" polypeptide is a polypeptide free from other biological macromolecules and at least 65% (e.g., at least 70, 75, 80, 85, 90, 95, or 99%) pure by dry weight. The purity of a polypeptide can be measured by any appropriate standard method, for example, by column chromatography, polyacrylamide gel electrophoresis, or HPLC analysis. The lactoferrin polypeptide can be a naturally occurring polypeptide, a recombinant polypeptide, or a synthetic polypeptide. Variants of a wild-type lactoferrin polypeptide (e.g., a fragment of the wild-type lactoferrin polypeptide containing at least 2 (e.g., 4, 6, 8, 10, 20, 50, 100, 200, 300, 400, 500, 600, 700) amino acids, or a recombinant protein containing a lactoferrin polypeptide sequence) that maintain the biological activity of a wild-type lactoferrin polypeptide are within the scope of the invention. A lactoferrin polypeptide of the invention can be of a mammalian origin, e.g., from human or bovine milk. The metal ion bound to the polypeptide can be an iron ion (as in a naturally occurring lactoferrin polypeptide), a copper ion, a chromium ion, a cobalt ion, a manganese ion, a zinc ion, or a magnesium ion.

A lactoferrin polypeptide of the invention can be used to stimulate skeletal growth (e.g., by promoting proliferation of osteoblasts and chondrocytes) and inhibit bone resorption (e.g., by inhibiting osteoclast development). A preparation of a lactoferrin polypeptide of the invention (e.g., lactoferrin isolated from bovine milk) can contain polypeptides of a single species, e.g., every molecule binding two iron ions. It can also contain polypeptides of different species, e.g., some molecules binding no ion and others each binding one or two ions; some molecules each binding an iron ion and others each binding a copper ion; some molecules each being a biological active lactoferrin polypeptide (full-length or shorter than full-length) that contains 0, 1, or 2 metal ions and others each being a fragment (same or different) of the polypeptide; or all molecules each being a fragment (same or different) of a full-length lactoferrin polypeptide that contains 0, 1, or 2 metal ions. For example, a mixture of full-length lactoferrin polypeptides and various fragments of full-length lactoferrin polypeptides can be prepared from a hydrolysate, e.g., a partial digest such as a proteinase digest, of full-length lactoferrin polypeptides. Otherwise, it can be obtained by mixing full-length lactoferrin polypeptides with various fragments of full-length lactoferrin polypeptides (e.g., synthetic fragments). A mixture of various fragments of fall-length lactoferrin polypeptides, on the other hand, can be prepared, for example, by complete digestion (i.e., no full-length polypeptides remain after digestion) of full-length lactoferrin polypeptides, or by mixing different fragments of full-length lactoferrin polypeptides.

The invention further features a nutraceutical composition, which can be milk, juice, a soft drink, a snack bar, or a dietary supplement. The nutraceutical composition contains a lactoferrin polypeptide of the invention or a mixture of the polypeptide and fragments of the polypeptide in an amount higher than the naturally occurring amount. Lactoferrin has been found to stimulate osteoblast and chondrocyte proliferation and inhibit osteoclast development. Thus, a nutraceutical composition of this invention is useful for preventing and treating bone disorders such as osteoporosis and rheumatoid or osteo-arthritis. The nutraceutical composition can further include an adequate amount of another bone-enhancing agent, such as calcium, zinc, magnesium, vitamin C, vitamin D, vitamin E, vitamin K2, or a mixture thereof.

In addition, this invention features a pharmaceutical composition that contains a lactoferrin polypeptide of the invention or a mixture of the polypeptide and fragments of the polypeptide and a pharmaceutically acceptable carrier. Optionally, the pharmaceutical composition also includes another bone-enhancing agent. The invention also encompasses the use of a lactoferrin polypeptide or a mixture of the polypeptide and fragments of the polypeptide described above for the manufacture of a medicament for preventing and treating bone diseases.

This invention provides a method of preventing and treating bone-related disorders (e.g., by stimulating skeletal growth and inhibiting bone resorption). The method includes administering to a subject in need thereof an effective amount of a lactoferrin polypeptide of the invention or a mixture of the polypeptide and fragments of the polypeptide. The method can further include concurrently administering to the subject an effective amount of another bone-enhancing agent.

The details of one or more embodiments of the invention are set forth in the accompanying description below. Other features, objects, and advantages of the invention will be apparent from the detailed description, and from the claims.

DETAILED DESCRIPTION

This invention is based on the unexpected discovery that lactoferrin stimulates osteoblast and chondrocyte proliferation and inhibits osteoclast development. Thus, it is useful for preventing and treating bone disorders.

A lactoferrin polypeptide of the invention is a pure polypeptide containing no more than two metal ions per molecule. Practically, the measurement of the ion/lactoferrin ratio for a preparation of lactoferrin can be in the range of 0-2.5. It can be isolated from a natural source (e.g., mammalian milk), or produced using genetic engineering or chemical synthesis techniques well-known in the art. The following is an exemplary procedure for isolating lactoferrin from bovine milk:

Fresh skim milk (7 L, pH 6.5) is passed through a 300 ml column of S Sepharose Fast Flow equilibrated in milli Q water, at a flow rate of 5 ml/min and at 4° C. Unbound protein is washed through with 2.5 bed volumes of water and bound protein eluted stepwise with approximately 2.5 bed volumes each of 0.1 M, 0.35 M, and 1.0 M sodium chloride. Lactoferrin eluting as a discreet pink band in 1 M sodium chloride is collected as a single fraction and dialysed against milli Q water followed by freeze-drying. The freeze-dried powder is dissolved in 25 mM sodium phosphate buffer, pH 6.5 and subjected to rechromatography on S Sepharose Fast Flow with a sodium chloride gradient to 1 M in the above buffer and at a flow rate of 3 ml/min. Fractions containing lactoferrin of sufficient purity as determined by gel electrophoresis and reversed phase HPLC are combined, dialyzed and freeze-dried. Final purification of lactoferrin is accomplished by gel filtration on Sephacryl 300 in 80 mM dipotassium phosphate, pH 8.6, containing 0.15 M potassium chloride. Selected fractions are combined, dialyzed against milli Q water, and freeze-dried. The purity of this preparation is greater than 95% as indicated by HPLC analysis and by the spectral ratio values (280 nm/465 nm) of ~19 or less for the iron-saturated form of lactoferrin.

Iron saturation is achieved by addition of a 2:1 molar excess of 5 mM ferric nitrilotriacetate (Foley and Bates (1987) Analytical Biochemistry 162, 296-300) to a 1% solution of the purified lactoferrin in 50 mM Tris, pH 7.8 containing 10 mM sodium bicarbonate. Excess ferric nitrilotriacetate is removed by dialysis against 100 volumes of milli Q water (twice renewed) for a total of 20 hours at 4° C. The iron-loaded (holo-) lactoferrin is then freeze-dried.

Iron-depleted (apo-) lactoferrin is prepared by dialysis of a 1% solution of the highly purified lactoferrin sample in water against 30 volumes of 0.1 M citric acid, pH 2.3, containing 500 mg/L disodium EDTA, for 30 h at 4° C. (Massons and Heremans (1966) Protides of the Biological fluids 14, 115-124). Citrate and EDTA are then removed by dialysis against 30 volumes of milli Q water (once renewed) and the resulting colourless solution freeze-dried.

A lactoferrin polypeptide of the invention can contain an iron ion (as in a naturally occurring lasctoferrin polypeptide) or a non-iron metal ion (e.g., a copper ion, a chromium ion, a cobalt ion, a manganese ion, a zinc ion, or a magnesium ion). For instance, lactoferrin isolated from bovine milk can be depleted of iron and then loaded with another type of metal ion. For example, copper loading can be achieved according to the same method for iron loading described above. For loading lactoferrin with other metal ions, the method of Ainscough, et al. ((1979) Inorganica Chimica Acta 33, 149-153) can be used.

In a preparation of a lactoferrin polypeptide of the invention, the polypeptides can be of a single species, or of different species. For instance, the polypeptides can each contain a different number of metal ions or a different species of metal ions; or the lengths of the polypeptides can vary, e.g., some are full-length polypeptides and some are fragments, and the fragments can each represent a particular portion of a full-length polypeptide. Such a preparation can be obtained from a natural source or by mixing different lactoferrin polypeptide species. For example, a mixture of lactoferrin polypeptides of different lengths can be prepared by proteinase digestion (complete or partial) of full-length lactoferrin polypeptides. The degree of digestion can be controlled according to methods well known in the art, e.g., by manipulating the amount of proteinase or the time of incubation. A complete digestion produces a mixture of various fragments of full-length lactoferrin polypeptides; a partial digestion produces a mixture of full-length lactoferrin polypeptides and various fragments.

A lactoferrin polypeptide or a mixture of the polypeptide and fragments of the polypeptide described above is used to prepare a nutraceutical composition of this invention for preventing and treating bone-related disorders. Examples of such disorders include, but are not limited to, osteoporosis, rheumatoid or osteo-arthritis, hepatic osteodystrophy, osteomalacia, rickets, osteitis fibrosa cystica, renal osteodystrophy, osteosclerosis, osteopenia, fibrogenesis-imperfecta ossium, secondary hyperparathyrodism, hypoparathyroidism, hyperparathyroidism, chronic renal disease, sarcoidosis, glucocorticoid-induced osteoporosis, idiopathic hypercalcemia, Paget's disease, and osteogenesis imperfecta. The nutraceutical composition can be a dietary supplement (e.g., a capsule, a mini-bag, or a tablet) or a food product (e.g., milk, juice, a soft drink, a herbal tea-bag, or confectionary). The composition can also include other nutrients, such as a protein, a carbohydrate, vitamins, minerals, or amino acids. The composition can be in a form suitable for oral use, such as a tablet, a hard or soft capsule, an aqueous or oil suspension, or a syrup; or in a form suitable for parenteral use, such as an aqueous propylene glycol solution, or a buffered aqueous solution. The amount of the active ingredient in the nutraceutical composition depends to a large extent on a subject's specific need. The amount also varies, as recognized by those skilled in the art, dependent on administration route, and possible co-usage of other bone-enhancing agents.

Also within the scope of this invention is a pharmaceutical composition that contains an effective amount of a lactoferrin polypeptide or a mixture of the polypeptide and fragments of the polypeptide described above, and a pharmaceutically acceptable carrier. The pharmaceutical composition can be used to prevent and treat bone-related disorders described above. The pharmaceutical composition can further include an effective amount of another bone-enhancing agent. The pharmaceutically acceptable carrier includes a solvent, a dispersion medium, a coating, an antibacterial and antifungal agent, and an isotonic and absorption delaying agent. An "effective amount" is the amount required to confer therapeutic effect. The interrelationship of dosages for animals and humans (based on milligrams per meter squared of body surface) is described by Freireich, et al. (1966) Cancer Chemother. Rep. 50: 219. Body surface area can be approximately determined from height and weight of the subject. See, e.g., Scientific Tables, Geigy Pharmaceuticals, Ardley, N.Y., 1970, 537. Effective doses also vary, as recognized by those skilled in the art, dependent on route of administration, excipient usage, and the like.

A lactoferrin polypeptide of the invention or a mixture of the polypeptide and fragments of the polypeptide can be formulated into dosage forms for different administration routes utilizing conventional methods. For example, it can be formulated in a capsule, a gel seal, or a tablet for oral administration. Capsules can contain any standard pharmaceutically acceptable materials such as gelatin or cellulose. Tablets can be formulated in accordance with conventional procedures by compressing mixtures of the lactoferrin polypeptide or a mixture of the polypeptide and fragments of the polypeptide with a solid carrier and a lubricant. Examples of solid carriers include starch and sugar bentonite. The lactoferrin polypeptide or a mixture of the polypeptide and fragments of the polypeptide can also be administered in a form of a hard shell tablet or a capsule containing a binder, e.g., lactose or mannitol, a conventional filler, and a tableting agent. The pharmaceutical composition can be administered via the parenteral route. Examples of parenteral dosage forms include aqueous solutions, isotonic saline or 5% glucose of the active agent, or other well-known pharmaceutically acceptable excipient. Cyclodextrins, or other solubilizing agents well-known to those familiar with the art, can be utilized as pharmaceutical excipients for delivery of the therapeutic agent.

The efficacy of a composition of this invention can be evaluated both in vitro and in vivo. See, e.g., the examples below. Briefly, the composition can be tested for its ability to promote osteoblast and chondrocyte proliferation in vitro. For in vivo studies, the composition can be injected into an animal (e.g., a mouse) and its effects on bone tissues are then accessed. Based on the results, an appropriate dosage range and administration route can be determined.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

Lactoferrin Promotes Proliferation of Primary Rat Osteoblasts

Osteoblasts were isolated by collagenase digestion from 20-day fetal rat calvariae, as previously described by Lowe and co-workers (Lowe, et al. (1991) Journal of Bone and Mineral Research 6, 1277-1283). Calvariae were dissected aseptically, and the frontal and parietal bones were stripped of their periosteum. Only the central portions of the bones, free from suture tissue, were collected. The calvariae were treated twice with phosphate buffered saline (PBS) containing 3 mM EDTA (pH 7.4) for 15 minutes at 37° C. in a shaking water bath. After washing once in PBS, the calvariae were treated twice with 3 ml of 1 mg/ml collagenase for 7 minutes at 37° C. After discarding the supernatants from digestions I and II, the calvariae were treated further two times with 3 ml of 2 mg/ml collagenase (30 mins, 37° C.). The supernatants of digestions III and IV were pooled, centrifuged, and the cells washed in Dulbecco's modified Eagle's medium (DME) with 10% fetal calf serum (FCS), suspended in DME/10% FCS, and placed in 75 cm$^3$ flasks. The cells were incubated under 5% $CO_2$ and 95% air at 37° C. Confluence was reached by 5-6 days, at which time the cells were subcultured. After trypsinization using trypsin-EDTA (0.05%/0.53 mM), the cells were rinsed in minimum essential medium (MEM) with 5% FCS and resuspended in a fresh medium, then seeded at $5 \times 10^4$ cells/ml in 24-well plates (0.5 ml cell suspension per well, i.e., $1.4 \times 10^4$ cells/cm$^2$). The osteoblast-like character of these cells has been established by demonstration of high levels of alkaline phosphatase activity and osteocalcin production [as described by Groot, et al. (1985) Cell Biol Int Res 9, 528] and a sensitive adenylate cyclase response to parathyroid hormone and prostaglandins [as described by Hermann-Erlee, et al. (1986) Ninth International Conference on calcium regulating hormones and bone metabolism, p 409].

Proliferation studies (cell counts and thymidine incorporation) were performed both in actively growing and non-actively growing cell populations. To produce actively growing cells, sub-confluent populations (24 h after subculturing) were placed in fresh MEM containing 1% FCS and a lactoferrin sample. To produce non-actively growing cells, sub-confluent populations were placed in serum-free medium with 0.1% bovine serum albumin plus a lactoferrin sample. Cell numbers were analyzed at 6, 24, and 48 hours after the addition of lactoferrin samples (i.e., purified lactoferrin, holo-lactoferrin, and apo-lactoferrin) prepared as described above. The cell numbers were determined after detaching cells from the wells by exposure to trypsin/EDTA (0.05%/0.53 mM) for approximately 5 minutes at 37° C. Counting was performed in a haemocytometer chamber. [$^3$H]-thymidine incorporation into actively growing and non-actively growing cells was assessed by pulsing the cells with [$^3$H]-thymidine (1 μCi/well) two hours before the end of the incubation. The experiment was terminated at 6, 24, or 48 hours by washing the cells in MEM containing cold thymidine followed by the addition of 10% trichloroacetic acid. The precipitate was washed twice with ethanol:ether (3:1), and the wells desiccated at room temperature. The residue was redissolved in 2 M KOH at 55° C. for 30 min, neutralized with 1 M HCl, and an aliquot counted for radioactivity. For both cell counts and thymidine incorporation, each experiment at each time point was performed at least 4 different times using experimental groups consisting of at least 6 wells.

The mitogenic response of the purified lactoferrin sample was found to be very potent, as shown by a markedly increased rate of osteoblast cell proliferation (i.e., increase in thymidine incorporation into DNA of growing cells). The potent osteogenic response seen above was compared with that of insulin-like growth factor 1 (IGF-1), a well-recognized osteoblast mitogen. IGF-1 showed a maximal effect of 1.25 times the control in the same osteoblast cell culture system, whereas lactoferrin's effect was 2.26 times that of the control for the highest dose tested (10 μg/ml).

Lactoferrin Promotes Proliferation of Chondrocytes

Chondrocytes were isolated by removing cartilage (full-depth slices) from the tibial and femoral surfaces of sheep under aseptic conditions. Slices were placed in Dulbecco's Modified Eagles (DME) media containing 5% FBS (v/v) and antibiotics (penicillin 50 g/L, streptomycin 50 g/L and neomycin 100 g/L) and chopped finely with a scalpel blade. Tissue was removed and incubated at 37° C. with firstly pronase (0.8% w/v for 90 minutes) followed by collagenase (0.1% w/v for 18 hours) to complete the digestion. Cells were isolated from the digest by centrifugation (10 minutes at 1300 rpm), resuspended in DME/5% FBS, passed through a nylon mesh screen of 90 Fm pore size to remove any undigested fragments, and recentrifuged. The cells were then washed and resuspended twice in the same media, seeded into a 75 cm$^2$ flask containing DME/10% FBS, and incubated under 5% $CO^2$/95% air at 37° C. Confluence was reached by 7 days, at which time the cells were subcultured. After trypsinization using trypsin-EDTA (0.05%/0.53 mM), the cells were rinsed in DME/5% FBS and resuspended in a fresh medium, then seeded into 24-well plates ($5 \times 10^4$ cells/mL, 0.5 mL/well). Measurement of thymidine incorporation was performed in growth-arrested cell populations as for the osteoblast-like cell cultures described above. Lactoferrin was found to stimulate chondrocyte proliferation at concentrations above 0.1 μg/ml.

Lactoferrin Promotes Proliferation of Osteoblasts in Organ Culture

Neonatal mouse organ culture has been previously described (Cornish, et al. (1998) Am J Physiol 274, E827-E833). Briefly, two-day old neonatal mice were subcutaneously injected with radioactively labeled $^{45}$Ca. Three days later, the calvariae were excised and placed on mesh grids in Petri dishes containing 0.1% bovine serum albumin/Media 199. Lactoferrin was added, and the calvariae were incubated for 48 hours. Four hours before the end of the incubation period, [$^3$H]-thymidine was added. The experiment was terminated, and $^{45}$Ca release and thymidine incorporation were measured. Lactoferrin was found to stimulate DNA synthesis, which reflects the proliferation of cells of the osteoblast lineage.

Lactoferrin Signals Via MAP Kinase in Osteoblasts

This methodology has been previously described (Grey, et al. (2001) Endocrinology 142, 1098-1106). Specifically, primary rat osteoblasts prepared as described above were seeded in 6-well tissue culture plates at an initial density of $5 \times 10^4$ cells/ml in MEM 5% FCS, and grown to 80-90% confluence. After serum starvation overnight, cells were treated at room temperature with lactoferrin in MEM/0.1% BSA. In experiments designed to determine the effect of inhibitors of signal transduction on lactoferrin-induced p42/44 MAP kinase phosphorylation, the cells were pre-treated with the inhibitor for 30 min prior to addition of lactoferrin. After treatment for the indicated period of time, the treatment medium was aspirated, the cells were washed in ice-cold PBS and then scraped in ice-cold HNTG lysis buffer (50 mM HEPES, pH 7.5, 150 mM NaCl, 1% Triton, 10% glycerol, 1.5 mM $MgCl_2$, 1 mM EDTA) containing a cocktail of protease and phosphatase inhibitors (1 mM PMSF, 1 μg/ml peptatin, 10 μg/ml leupeptin, 10 μg/ml aprotinin, 1 mM sodium vanadate, 500 mM NaF). The lysates were briefly vortexed, centrifuged at 13,000 rpm at 4° C., then stored at −70° C. until analyzed. Protein content of the cell lysates was measured using the DC protein assay (BioRad, Hercules, Calif.). Equal amounts of the whole cell lysate (30-50 μg) were subjected to 8% SDS-PAGE, transferred to nitrocellulose membranes, and immunoblotted overnight at 4° C. with an anti-phospho-p42/44 MAP kinase antibody (1:1000). As a control for protein loading, the same filters were stripped and re-probed with an antibody against total p42/44 MAP kinase (1:400). Incubation with the HRP-conjugated secondary antibody was for 1 h at room temperature, and the membranes were analyied by ECL. Immunoblots were repeated at least 3 times. Lactoferrin was found to induce phosphorylation of p42/p44 MAP kinases in osteoblasts in a dose- and time-dependent manner at concentrations of 1-100

Lactoferrin Stimulates Bone Growth In Vivo

The mouse model used in these studies have been previously described (Cornish, et al. (1993) Endocrinology 132, 1359-1366). Injections (0 mg, 0.04 mg, 0.4 mg and 4 mg) of lactoferrin were given daily for 5 days, and the animals were sacrificed one week later. Bone formation was determined by fluorescent labeling of newly formed bone. Indices of bone resorption and of bone mass were determined by conventional light microscopy, assisted by image analysis software. Local injection of lactoferrin in adult mice resulted in increased calvarial bone growth, with significant increases in bone area after only 5 injections.

Application 1

Set yoghurts of between 14 and 17% solids, with or without fruit added, can be prepared as follows:

Medium heat skim milk powder (between 109-152 g) and ALACO stabilizer (100 g) are reconstituted with approximately 880 ml of 50° C. water. Anhydrous Milk Fat (20 g) is then added and mixed for 30 min. The mixture is then heated to 60° C., homogenized at 200 bar, and then pasteurized at 90° C. After cooling to a temperature between 40-42° C., a starter mixture and the freeze-dried protein preparation described above (up to 50 mg of lactoferrin at 95% purity or an equivalent quantity from a not so highly purified source) is added. If desired, fresh fruit may also be added at this point. The mixture is then filled into containers, incubated at 40° C. until pH 4.2-4.4 is reached, and then chilled in a blast cooler.

An alternative method for preparing the same set yoghurts is by dry blending the indicated quantity of lactoferrin or the indicated quantity as a dose rate, into the dry milk solids, prior to its use in the yoghurt formulation.

Application 2

Dry blends of either skim or whole milk powder with calcium and the freeze dried lactoferrin preparations can give dairy based formulations or compositions which can be used either as functional foods or as functional food ingredients. Such compositions can be used as reconstituted milks, milk powder ingredients, dairy desserts, functional foods, cheeses or butter or beverages, and nutraceuticals or dietary supplements. Blending the dry ingredients in ratios of milk powder:calcium:active lactoferrin agent between 90:9.5:0.5 and 94:5.95:0.0001 provide compositions suitable for such uses.

Application 3

Blended compositions of milk powder, calcium, and the lactoferrin rich ingredient can be used as bone health functional foods, bone health food ingredients, or as a food ingredient for delivery of bone health nutrients in a range of health foods.

For such compositions, the calcium and protein contents of the compositions need to be adjusted to required, allowable nutritional limits. Commercially available ingredient milk powders typically contains between 300 and 900 mg calcium per 100 g powder, depending upon their sources. A source of calcium may be added to the powder to extend the calcium content up to 3% by weight of the ingredient milk powder as a blend. The protein level of commercially available ingredient milk or dairy-based protein powders varies depending upon the type of the ingredient, the method of its manufacture, and its intended use. Ingredient milk powder typically contains between 12% and 92% protein. Examples are commercially available skim and whole milk powders, food grade caseins, caseinates, milk protein concentrate powders, spray dried ultrafiltered or microfiltered retentate powders, and the milk protein isolate products. The lactoferrin rich preparation may be incorporated into a protein and calcium blend to give nutritional milk powders that can be used as ingredients in healthy foods and drinks. Such blends provide ingredients suitable for use in preparing yoghurts and yoghurt drinks, acid beverages, ingredient milk powder blends, pasteurized liquid milk products, UHT milk products, cultured milk products, acidified milk drinks, milk-and-cereal combination products, malted milks, milk-and-soy combination products. For such uses, the blend can have a composition where the calcium content is between 0.001% and 3.5% (w/w), the protein composition is between 2% and 92%, and lactoferrin as the osteoblast proliferating agent is added at levels between 0.000001% and 5.5%.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of treating osteoporosis, the method comprising administration of a composition consisting essentially of at least 65% lactoferrin polypeptide by dry weight, as the active agent, to a subject in need thereof, wherein the lactoferrin in the composition contains no more than two metal ions per molecule of lactoferrin polypeptide.

2. The method of claim 1, wherein the lactoferrin polypeptide is apo-lactoferrin.

3. The method of claim 1, wherein the lactoferrin polypeptide contains one metal ion per molecule.

4. The method of claim 3, wherein the lactoferrin polypeptide contains iron, copper, chromium, cobalt, manganese, zinc, or magnesium ion.

5. The method of claim 4, wherein the lactoferrin polypeptide contains an iron ion.

6. The method of claim 1, wherein the lactoferrin polypeptide contains two metal ions per molecule.

7. The method of claim 6, wherein the lactoferrin polypeptide contains iron, copper, chromium, cobalt, manganese, zinc, or magnesium ions.

8. The method of claim 7, wherein the lactoferrin polypeptide contains iron ions.

9. The method of claim 1, wherein the lactoferrin polypeptide is human.

10. The method of claim 1, wherein the lactoferrin polypeptide is recombinant.

11. The method of claim 1, wherein the lactoferrin polypeptide is at least 75% pure.

12. The method of claim 7, wherein the lactoferrin polypeptide is at least 85% pure.

13. The method of claim 8, wherein the lactoferrin polypeptide is at least 95% pure.

14. The method of claim 1, wherein the composition is a nutraceutical composition.

15. The method of claim 1, wherein the composition is a pharmaceutical composition.

16. The method of claim 1, further comprising co-administration of an additional bone enhancing agent.

17. The method of claim 16, wherein said bone enhancing agent is selected from calcium, zinc, magnesium, vitamin C, vitamin D, vitamin E and vitamin K2.

18. The method of claim 1 wherein the pharmaceutical composition consisting essentially of at least 65% lactoferrin polypeptide by dry weight, as the active agent, further comprises a pharmaceutically acceptable carrier.

* * * * *